(12) United States Patent
Choong

(10) Patent No.: US 10,325,765 B2
(45) Date of Patent: Jun. 18, 2019

(54) SYSTEMS AND METHODS FOR AMBIENT SURFACE CLEANING AND SAMPLING WITH MASS SPECTROMETRIC ANALYSIS

(71) Applicant: Purdue Research Foundation, West Lafayette, IN (US)

(72) Inventor: Shi Wah Choong, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 4 days.

(21) Appl. No.: 15/726,896

(22) Filed: Oct. 6, 2017

(65) Prior Publication Data

US 2018/0102242 A1 Apr. 12, 2018

Related U.S. Application Data

(60) Provisional application No. 62/404,942, filed on Oct. 6, 2016.

(51) Int. Cl.
*H01J 49/26* (2006.01)
*H01J 49/00* (2006.01)
(Continued)

(52) U.S. Cl.
CPC ............ *H01J 49/0031* (2013.01); *B08B 9/46* (2013.01); *H01J 49/0013* (2013.01); *H01J 49/0409* (2013.01); *G01N 2001/028* (2013.01)

(58) Field of Classification Search
CPC ............... H01J 49/0431; H01J 49/0409; H01J 49/0031; G01N 2001/28
See application file for complete search history.

(56) References Cited

U.S. PATENT DOCUMENTS 7,015,466 B2 3/2006 Cooks
8,410,431 B2 4/2013 Ouyang
(Continued)

FOREIGN PATENT DOCUMENTS

WO WO 2014120411 A1 * 8/2014 ............ H01J 49/167

OTHER PUBLICATIONS

FDA, Guidance for Industry, Analytical Procedures and Methods Validation for Drugs and Biologics (Jul. 2015).
(Continued)

*Primary Examiner* — Eliza W Osenbaugh-Stewar
(74) *Attorney, Agent, or Firm* — Purdue Research Foundation; Liang Zeng Yan

(57) ABSTRACT

The invention generally relates to systems and methods for continuous or batch wise sampling of a surface for analysis of trace chemical constituents that may be present on the surface by mass spectrometry. Integration of time and place of the sampling and analysis processes allows real-time on-the-spot response to the analytical data and can take into account that material is not necessarily uniformly distributed on a surface. A further feature of the systems and methods of the invention is that the swabbing process also cleans the surface being analyzed. Accordingly, systems and methods of the invention provide an integrated approach that allows for a surface to be cleaned, sampled and analyzed in real-time, providing a faster and more efficient way to verify or validate whether a manufacturing vessel is sufficiently clean to start another production.

10 Claims, 13 Drawing Sheets

(51) Int. Cl.
*B08B 9/46* (2006.01)
*H01J 49/04* (2006.01)
*G01N 1/02* (2006.01)

(56) References Cited

U.S. PATENT DOCUMENTS

2012/0119079 A1    5/2012  Ouyang
2013/0280819 A1   10/2013  Cooks
2014/0249451 A1*   9/2014  Mao .................. A61B 10/0045
                                              600/583

OTHER PUBLICATIONS

Pawar, H.A., et al., "Current Perspectives on Cleaning Validation in Pharmaceutical Industry: A Scientific and Risk Based Approach." Int. J. Pharm. Phytopharmacol. Res. 2011, 1(1): 8-16.
Soparawalla, S., et al., "Pharmaceutical cleaning validation using non-proximate large-area desorption electrospray ionization mass spectrometry." Rapid Commun. Mass Spectrom. 2009; 23: 131-137.

* cited by examiner

SYSTEMS AND METHODS FOR AMBIENT SURFACE CLEANING AND SAMPLING WITH MASS SPECTROMETRIC ANALYSIS

CROSS-REFERENCE TO RELATED APPLICATIONS

The present U.S. patent application is related to and claims the priority benefit of U.S. Provisional Patent Application Ser. No. 62/404,942, filed Oct. 6, 2016, the contents of which are hereby incorporated by reference in their entirety into this disclosure.

TECHNICAL FIELD

The invention generally relates to systems and methods for continuous or batch-wise sampling of a surface for analysis of trace chemical constituents that may be present on the surface by mass spectrometry. Integration of time and place of the sampling and analysis processes allows real-time on-the-spot validation and verification of a cleaning process.

BACKGROUNDS

This section introduces aspects that may help facilitate a better understanding of the disclosure. Accordingly, these statements are to be read in this light and are not to be understood as admissions about what is or is not prior art.

In the production of pharmaceutical products, there is strong potential for batch contamination related to the presence of residual materials such as active ingredients, cleaning agents, microorganisms, dust and particulates. Cleaning validation provides documented evidence that the cleaning processes used have cleaned to predefined limits. The goal is to prevent contamination that can influence the safety, efficacy, purity and quality of manufactured products.

After the production process, the reaction or mixing vessel is cleaned by a prescribed method that may involve a series of solvents and/or cleaning agents or acidic, alkaline and/or surfactant solutions. Any one of those may leave residual material, and there could be an accumulation of materials on the surface once the "cleaning" process is complete. Pharmaceutical organizations must determine whether residual materials are present, and if so, how are they are represented on the surface. One of the most common surfaces is stainless steel and the characteristics of that surface (polished or brushed or roughened) can dictate how the materials adhere. Laboratory experiments with cleaned brushed stainless steel surfaces have indicated that residues from solid compounds deposited from solvents tend to exist as "islands" of material and not a continuous thin coating, due to the coalescing of materials during the evaporation process and nucleation around surface features and "dust particles".

It is essential to avoid cross-contamination during the manufacture of active pharmaceutical ingredients. Significant costs are associated with cleaning large reaction vessels used to prepare these substances and even greater costs in validating their cleanliness. The FDA has approved certain procedures for validation which involve manual swabbing and then liquid chromatography/mass spectrometry analysis of the swabbed materials ("Guidance for Industry: Analytical Procedures and Methods Validation for Drugs and Biologics", FDA, Rockville, Md., 2014). Large areas must be examined and the off-line mass spectrometry analysis is time-consuming (K Burson, et al., *Pharmaceutical Technology*, 2014). The lack of association of the cleaning/sampling step with the analytical step, in time and in place, is a significant problem with this approach (H. A. Pawar, et al., *Int. J. Pharm. Phytopharmacol. Res.* 1 (2011) 8-16). Attempts have been made to perform ambient ionization, specifically desorption electrospray ionization, on surfaces and to use this method to validate cleaning (S. Soparawalla, et al., *Rapid Commun. Mass Sepctrom.* 23 (2009), 131-137). However, there has been limited success with this approach. The described methods are cost intensive techniques that provide an averaged or integrated result and do not necessarily represent the surface or how materials are distributed over the surface.

SUMMARY OF THE INVENTION

The invention relates to systems and methods for continuous or batch wise sampling of a surface for analysis of trace chemical constituents that may be present on the surface by mass spectrometry. Integration of time and place of the sampling and analysis processes allows real-time on-the-spot validation and verification of a cleaning process. A further feature of the systems and methods of the invention is that the swabbing process also cleans the surface being analyzed. Accordingly, systems and methods of the invention provide an integrated approach that allows for a surface to be cleaned, sampled and analyzed in real-time, providing a faster and more efficient way to verify or validate whether a manufacturing vessel is sufficiently clean to start another production.

In some embodiments, the present invention relates to a system for analyzing an analyte from a surface, the system comprising:
  a. a surface interface member, the member comprising a portion that is configured to receive and retain a porous material that can absorb an analyte from a surface;
  b. a mass spectrometry probe;
  c. a transfer member that operably couples the surface interface member and the mass spectrometry probe; and
  d. a pump operably coupled to the system such that a vacuum pressure generated by the pump transfers an analyte absorbed on the porous material through the transfer line to the mass spectrometry probe.

In some embodiments, the present invention relates to a system for analyzing an analyte from a surface, wherein the porous material is a wetted porous material.

In some embodiments, the present invention relates to a system for analyzing an analyte from a surface disclosed herein, wherein the system further comprises a solvent reservoir operably coupled to the surface interface member to thereby supply solvent to the porous material.

In some embodiments, the present invention relates to a system for analyzing an analyte from a surface disclosed herein, wherein the porous material is temporarily retained on the surface interface member.

In some embodiments, the present invention relates to a system for analyzing an analyte from a surface disclosed herein, wherein the transfer member comprises a splitter that splits a portion of flow through the transfer member to the mass spectrometry probe while a remainder of flow is directed to a receiving vessel.

In some embodiments, the present invention relates to a system for analyzing an analyte from a surface disclosed herein, wherein the transfer member comprises a tube.

In some embodiments, the present invention relates to a system for analyzing an analyte from a surface disclosed herein, wherein the mass spectrometry probe is selected from the group consisting of: an electrospray probe, a nano electrospray probe, an atmospheric pressure chemical ionization probe, and a probe that generates ions by inductive charging wherein the use of an electric field for high voltage spray ionization is optional.

In some embodiments, the present invention relates to a system for analyzing an analyte from a surface disclosed herein, wherein the system further comprises a mass analyzer, which is part of a miniature mass spectrometer.

In some embodiments, the present invention relates to a validation and verification method for a cleaning process using the system disclosed herein, wherein absence of mass signals of a known contaminant validates and verifies said cleaning process.

In some embodiments, the present invention relates to a validation and verification method of a cleaning process for a surface using the system disclosed herein, wherein absence of mass signals of a known contaminant validates and verifies substantial cleanness of said surface.

In some other embodiments, the present invention relates to a method for analyzing an analyte from a surface, the method comprising:
a. contacting a surface interface member comprising a porous material to a surface to thereby absorb an analyte from the surface;
b. transferring the porous material containing analyte(s) of interest onto a mass spectrometer probe; and
c. analyzing the analyte by generating ions of the analyte via the mass spectrometry probe that are transferred to a mass analyzer.

In some embodiments, the present invention relates to a method for analyzing an analyte from a surface disclosed herein, wherein the transferring the porous material containing analyte(s) of interest is a continuous process or a stepwise operation.

In some embodiments, the present invention relates to a method for analyzing an analyte from a surface disclosed herein, wherein said contacting comprises swabbing the porous material of the surface interface member along at least a portion of the surface.

In some embodiments, the present invention relates to a method for analyzing an analyte from a surface disclosed herein, wherein prior to the contacting step, the method further comprises applying a solvent to the porous material.

In some embodiments, the present invention relates to a method for analyzing an analyte from a surface disclosed herein, wherein the analyzing method is performed onsite in real-time using a mass spectrometry.

In some embodiments, the present invention relates to a method for analyzing an analyte from a surface disclosed herein, wherein the method further comprises splitting the flow prior to the mass spectrometry probe such that only a portion of the flow is directed to the mass spectrometry probe.

In some embodiments, the present invention relates to a method for analyzing an analyte from a surface disclosed herein, wherein the mass spectrometry probe is selected from the group consisting of: an electrospray probe, a nano electrospray probe, an atmospheric pressure chemical ionization probe, and a probe that generates ions either by inductive charging or not.

In some embodiments, the present invention relates to a method for analyzing an analyte from a surface disclosed herein, wherein the mass analyzer is part of a miniature mass spectrometer.

In some embodiments, the present invention relates to a validation and verification method of a cleaning process for a surface, wherein absence of mass signals of a known contaminant validates and verifies said cleaning process.

In some embodiments, the present invention relates to a validation and verification method of a cleaning process for a surface, wherein absence of mass signals of a known contaminant validates and verifies substantial cleanness of said surface.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures, and wherein.

Figure 1A:
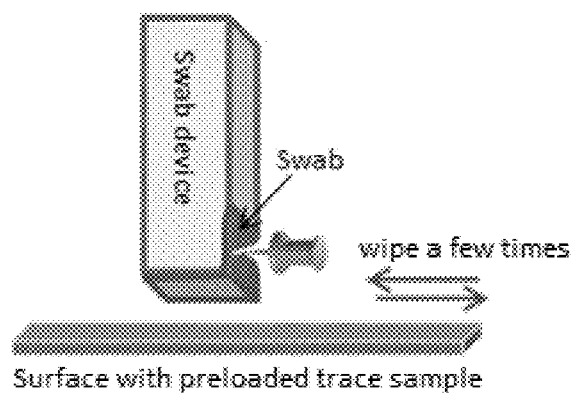
FIG. 1A is an illustration showing the scheme of an embodiment of the present disclosure, a small scale swab system, to achieve cleaning and sampling and direct analysis of a surface.

The attached drawings are for purposes of illustration and are not necessarily to scale.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range. In the present disclosure the term "substantially" can allow for a degree of variability in a value or range, for example, within 90%, within 95%, or within 99% of a stated value or of a stated limit of a range.

The invention generally relates to systems and methods for ambient surface cleaning and sampling with continuous mass spectrometric analysis. An exemplary device samples a surface using a wet swab and then uses peristaltic pump to transfer the analyte-containing solution from the swab into a receiving waste vessel. A flow splitter and waste-line help to ensure manageable adjustments to factors related to pressure changes when high flow rate solution is transferred into a chamber with low flow rate connected to an ionization source of a mass spectrometer.

FIG. 1A, FIG. 1B, 2, and FIG. 4 illustrate some embodiments of the present disclosure used to achieve cleaning, sampling and non-continuous analysis of a surface. This system includes a swabbing device to receive and retain a porous material can absorb an analyte from a surface. Exemplary porous material are described for example in Ouyang et al., (U.S. patent application publication number 2012/0119079), the content of which is incorporated by reference herein in its entirety. In certain embodiments, the porous material is fabric or filter paper.

The surface may be any surface, such as a bench-top or any obtain used in the production of chemicals, such as pharmaceutical chemicals. Exemplary objects include glassware and production vessels used in the process of manufacturing industrial chemicals, including active pharmaceutical ingredients (API). In other embodiments, the surface is that of a consumer product, such as an electronic device (smart phone, laptop computer, or tablet computer), an article of clothing (e.g., shoes, shirts, pants, shorts, or jacket), or a piece of luggage.

In certain embodiments, the porous material is a wetted porous material. The porous material can be wetted prior to or after placement on the surface interface member using various commonly used solvents in mass spectrometry, such as water, methanol, ethanol, acetonitrile, or a combination thereof. Wetting can be achieved using a pipette or any known way of delivery solvent to a surface. In certain embodiments, the surface is wetted with solvent and the dry porous material is contacted to the surface, thereby wetting the porous material. In other embodiments, the system includes a solvent reservoir that transfers solvent the porous material, thereby wetting the porous material.

Figure 1B:
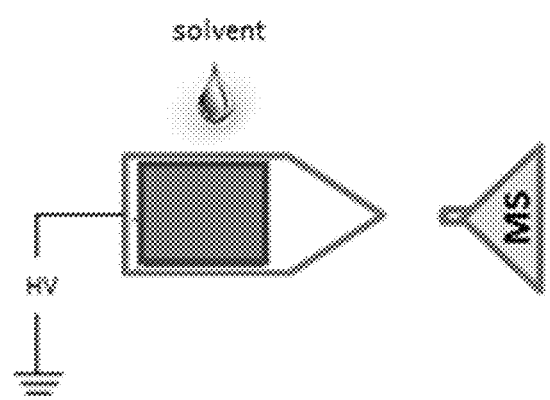
FIG. 1B is an illustration showing an embodiment of the surface interface member used to hold the porous material described in from FIG. 1A.
Figure 2:
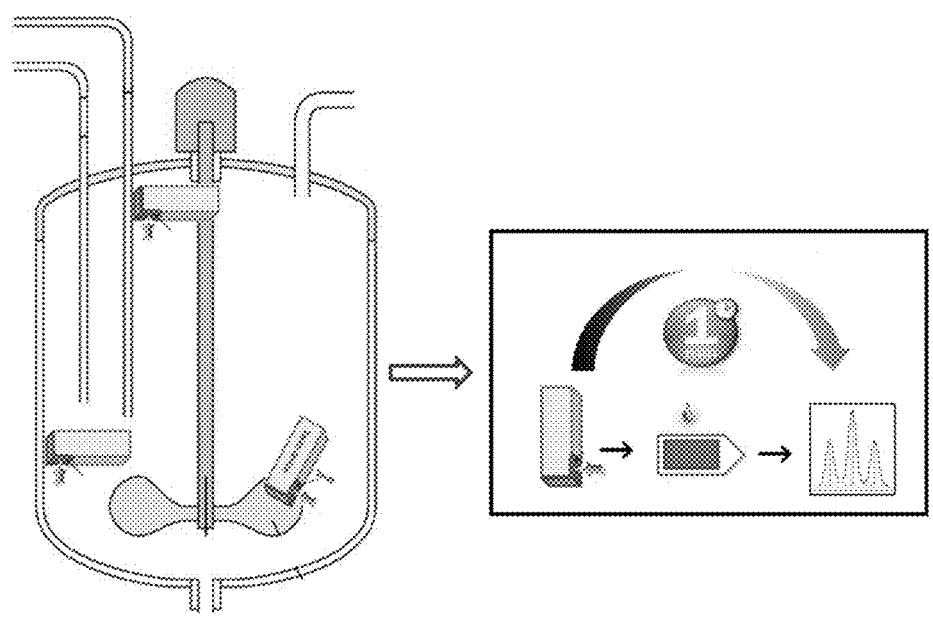
FIG. 2 depicts one embodiment and the advantages of this invention. A swab absorbs solvent and picks up residual contaminants directly, allowing onsite, real-time analysis with high specificity for an efficient cleaning validation.
Figure 4:
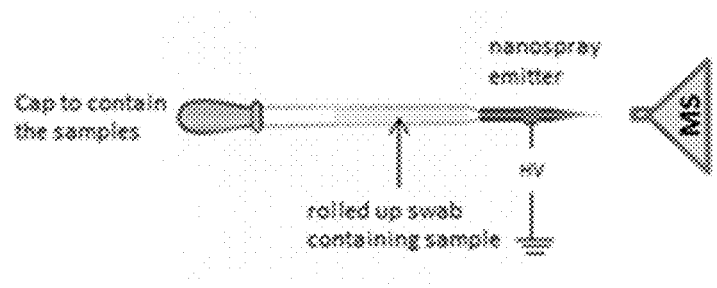
FIG. 4 is an illustration showing another embodiment of the present disclosure, a larger scale roll-and-spray system, to achieve cleaning and sampling and non-continuous analysis of a surface.

In certain embodiments, the porous material is temporarily retained on the surface interface member, i.e., is removable and disposable. Exemplary surface interface members are illustrated in FIG. 1B and FIG. 4. Typically, the porous material will be a disposable, one-time-use material, and after use, it is removed from the system and another piece of porous material is attached to the system.

The system also includes a mass spectrometry probe. Numerous different types of mass spectrometry probes can be used with systems of the invention. Exemplary probes include electrospray probes, electrosonic spray probes and nano-electrospray probes. In certain embodiments, the mass spectrometry probe is a probe that generates ions by inductive charging. Such probes are described for example in Cooks et al. (U.S. patent application publication number 2013/0280819 and U.S. Pat. No. 7,015,466), the content of which is incorporated by reference herein in its entirety. In some embodiments, such mass spectrometry probe includes a porous material to hold and transfer ions generated from fluids and solid samples. Such probes are described for example in Ouyang et al., (U.S. patent application publication number 2012/0119079). Briefly, such probes include spray emitter and a high voltage source, in which the probe is configured such that the high voltage source is not in contact with spray emitted by the spray emitter. In such a configuration, ions are generated by inductive charging. In some embodiments, the use of high voltage is not necessary. Mass spectra illustrated in FIG. 8-13 are collected with no use of high spray voltage.

Figure 6:
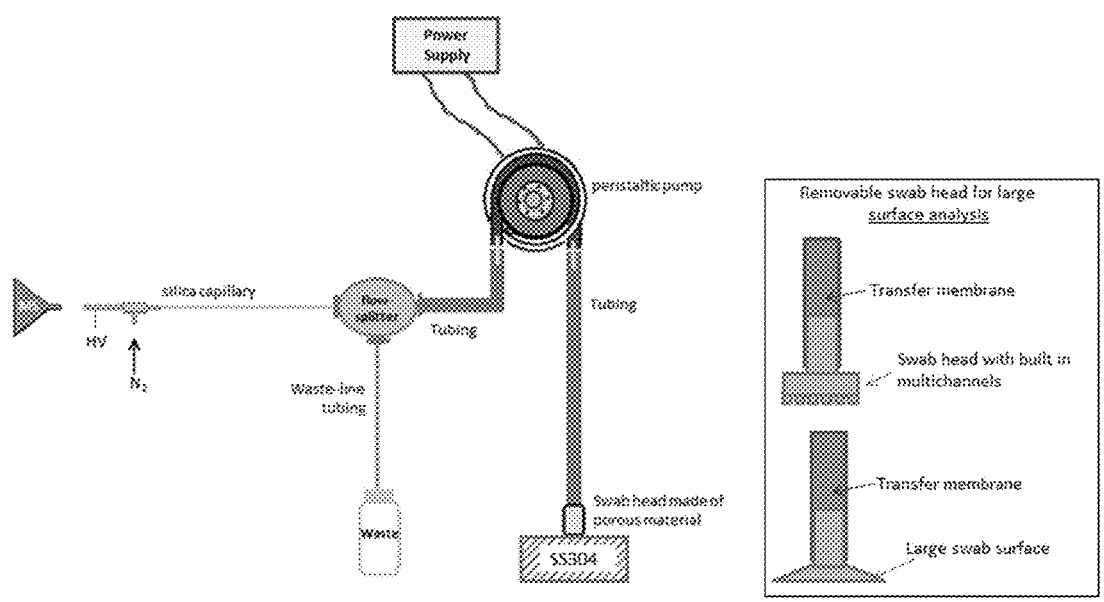
FIG. 6 is an illustration showing yet another embodiment of the present disclosure used to achieve cleaning, sampling and continuous online analysis of a surface.

The system illustrated in FIG. 6 also includes a transfer member that operably couples the surface interface member and the mass spectrometry probe. In certain embodiments, the transfer member is a tube. The tube may be composed of a rigid (e.g., glass or metal) or a flexible material (e.g., plastic or rubber). The tube may be straight or curved. Transfer members are further described for example in Ouyang et al. (U.S. Pat. No. 8,410,431), the content of which is incorporated by reference herein in its entirety. In certain embodiments, as shown in FIG. 6, the transfer member includes a splitter that splits a portion of flow through the transfer member to the mass spectrometry probe while a remainder of flow is directed to a receiving waste vessel. That vessel can be a waste vessel or some other type of vessel that is used to store the material captured from the surface. This captured material can be used for an orthogonal testing using another mass spectrometer or a non-mass-spectrometric analytical instrument.

The system also includes a pump operably coupled to the system such that a vacuum pressure generated by the pump transfers an analyte absorbed on the porous material through the transfer line to the mass spectrometry probe. Any type of pump known in the art may be used with systems of the invention. An exemplary pump is a peristaltic pump.

In certain embodiments, the system includes a mass analyzer. The mass analyzer may be part of a mass spectrometer. The mass spectrometer can be any type of mass spectrometer known in the art, and exemplary mass spectrometers are bench-top mass spectrometers and miniature mass spectrometers.

Systems of the invention can be used to analyze an analyte from a surface, such as a surface of an object used in the production of chemicals, such as pharmaceutical and forensic chemicals. The surface interface member is contacted to a surface in a manner in which the porous material on the surface interface member interacts with the surface. The porous material is wetted, either by solvent from the solvent reservoir or other wetting technique, which causes an analyte on the surface to be absorbed onto the porous material.

For systems illustrated in FIGS. 1A, 1B, 2 and 4, the analyte is collected on a piece of porous material, which is then transferred onto a mass spectrometric probe for analysis. For system illustrated in FIG. 6, the analyte is flowed from the porous material through the transfer member to the mass spectrometry probe that is coupled to the transfer member. The flowing is accomplished at least in part by a vacuum pressure created in the system by a pump operably coupled to the system. Additional solvent may be introduced into the system to facilitate the flow of the analyte to the mass spectrometry probe. The analyte is analyzed by generating ions of the analyte via the mass spectrometry probe that are transferred to a mass analyzer.

In certain embodiments, the contacting step involves swabbing the porous material of the surface interface member along at least a portion of the surface. The swabbing has the ability to clean the surface. The analysis happens in real-time. That is, the flowing and the analyzing step are continuous, and mass spectra are continuously generated. In certain embodiments, the collection of analyte and the analyzing step are not continuous.

Systems and methods of the invention integrate cleaning, sampling and chemical analysis. The systems and methods of the invention can be used to sample large surfaces. A removable swabbing head can be used to sample larger surfaces. In some embodiments, swabbing head with built-in channels help absorbing analytes over a larger surface. By transporting the solution through a narrow capillary tube, the distance between the site examined and the analytical instrument can be made large.

The swabbing can be automated, allowing the operator to remain outside the reactor with the instrument. Systems and methods of the invention allow immediate remediation action (further cleaning) in the event of impermissible levels of analyte. Swabs containing analytes can also be easily transported to different locations for extensive analyses. Systems and methods of the invention are well-suited to trace surface coverage and have the molecular specificity to characterize not only active pharmaceutical ingredients (API's) but also their degradation products. Systems and methods of the invention are also well-suited for trace surface analysis related to forensic products, food production, cosmetic and nutraceutical ingredients, household cleaning consumables, chemicals/biological contamination in diagnostics and medical devices, and electronic fabrication.

In some embodiments, this invention relates to a validation and verification method for a cleaning process according to the method disclosed herein, wherein absence of mass signals of a known contaminant validates said cleaning process.

In some other embodiments, this invention relates to a validation and verification method for a cleaning process using the mass spectroscopic system disclosed herein, wherein absence of mass signals of a known contaminant validates said cleaning process.

In some other embodiments, this invention relates to a validation and verification method Systems and methods of the invention can easily be multiplexed to look for a number of different analytes. Systems and methods of the invention can easily be made more specific by using multiple reaction monitoring (MRM) scans. Inductive ionization can be used to improve control of ionization period, to perform bipolar ionization, etc. Safety can be improved by automated cleaning and validation with continuous analytical readout. It is also possible to increase safety further by using a carbon nanotube (CNT) to lower voltage used for spray ionization from a surface.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

Example 1: Construction of a Small Scale Swab

Figure 3:
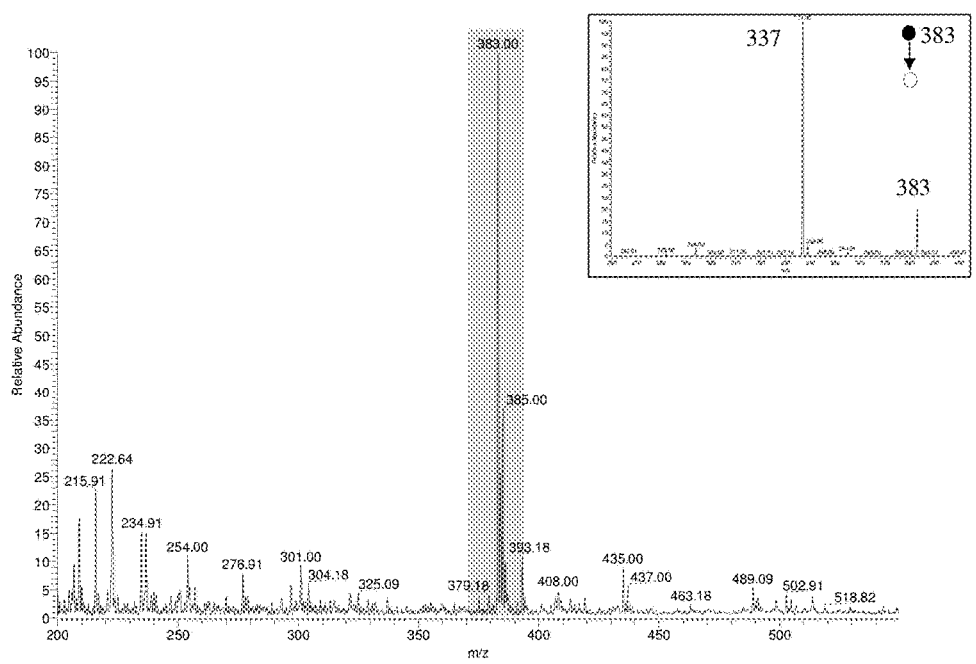
FIG. 3 is a full scan spectrum (Thermo LTQ) and MRM insert for trace surface analysis of Loratadine with m/z 383 on steel surface using the system of embodiments presented in FIG. 1A and FIG. 1B.

A 2 cm×2 cm×4 cm swab device was made using chemical resistant plastic. A piece of swab (2 cm×4 cm) was secured onto the swab device and this system was used as a swabbing tool (FIG. 1A). Trace sample ($10^{-12}$ to $10^{-6}$ gram) was pipetted onto 100 $cm^2$ stainless steel surface and allowed to air-dry. When the sample was dried, depends on the solvent the sample was dissolved in, usually in 1-10 minutes, about 100 uL solvent was used to wet the surface and the swabbing tool was used to wipe the area a few times to absorb the analyte. Then this piece of swab was cut and placed onto a paper spray probe for ambient mass spectrometric analysis (FIG. 1B). Analyte ions were detected when electric field (4.5 kV) was applied. Full and tandem mass spectra (FIG. 3) were collected using collision-induced dissociation (CID) to identify and confirm the analyte. Experiments were performed using Thermo Finnigan LTQ Mass Spectrometer.

Example 2: Roll-and-Spray Surface Analysis

Figure 5:
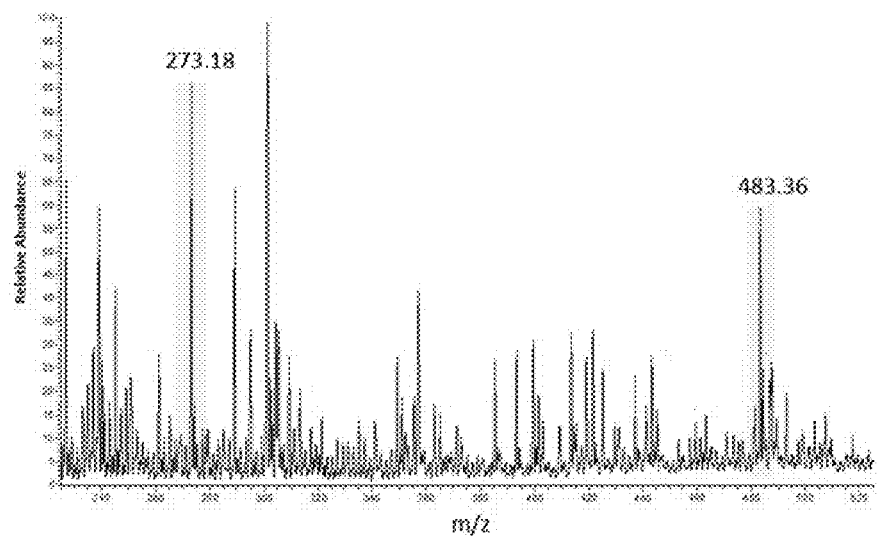
FIG. 5 is a full scan spectrum for two trace surface contaminants m/z 273 and 483 on steel surface using the system of embodiments illustrated in FIG. 1A and FIG. 4.

Similar to Example 1, this experiment was performed using a swab device (FIG. 4) with surface area of 10 $cm^2$ and sample was loaded onto a 250 $cm^2$ stainless steel surface. After the collection of the sample, the swab was rolled and inserted into a glass transfer member made of glass. About 500 uL solvent was applied into the spray emitter. Ions were generated using inductive nano-electrospray ionization. Full mass spectrum of a mixture of two analytes was collected (FIG. 5).

Example 3: Continuous Online Monitoring Surface Analysis

Figure 7:
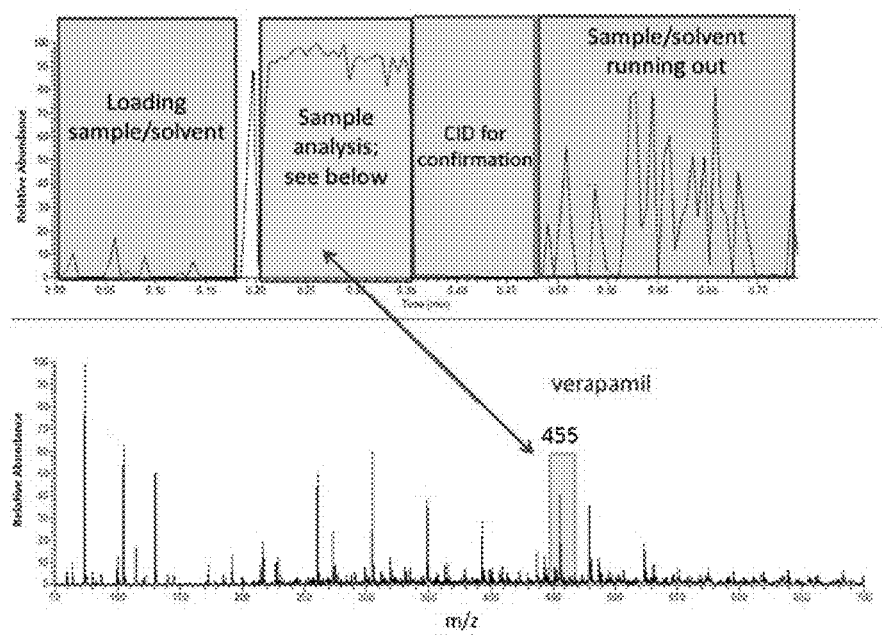
FIG. 7 is a time-based plot (chronograms) showing the schematic outline of an online analysis of trace contaminant (Verapamil) on a surface using the system of embodiment illustrated in FIG. 6.
Figure 8:
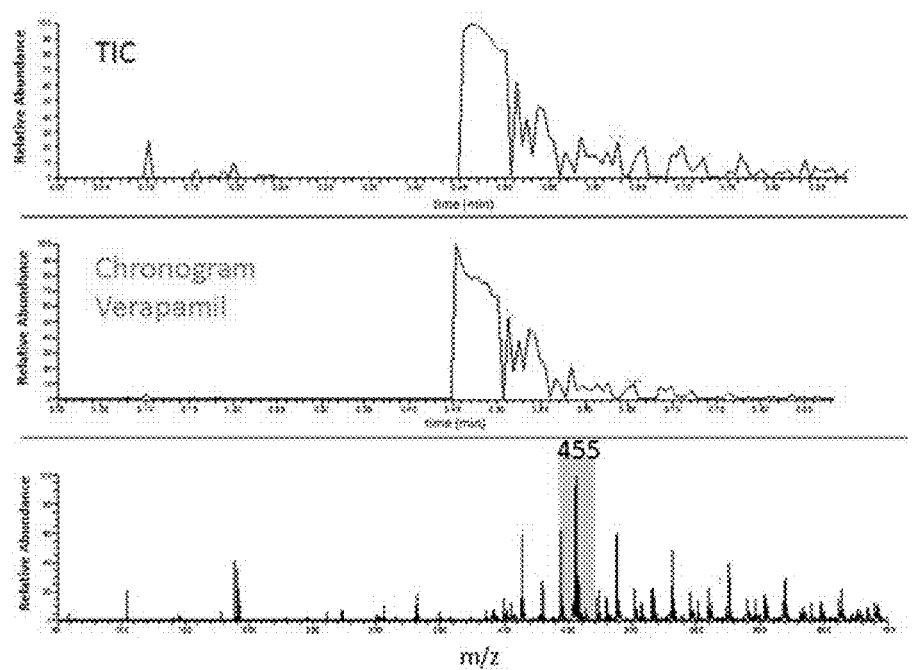
FIG. 8 shows a full mass spectrum of surface contaminant (0.05 ng/cm$^2$ Verapamil on stainless steel surface) using the embodiment illustrated in FIG. 6.
Figure 9:
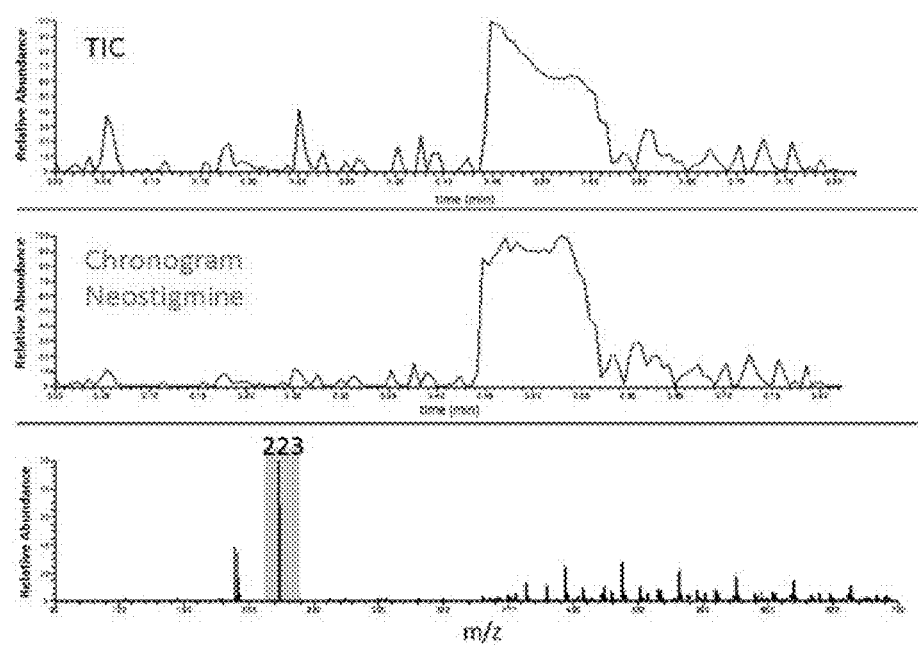
FIG. 9 shows a full mass spectrum of surface contaminant (12.5 pg/cm$^2$ Neostigmine on stainless steel surface) using the embodiment illustrated in FIG. 6.
Figure 10:
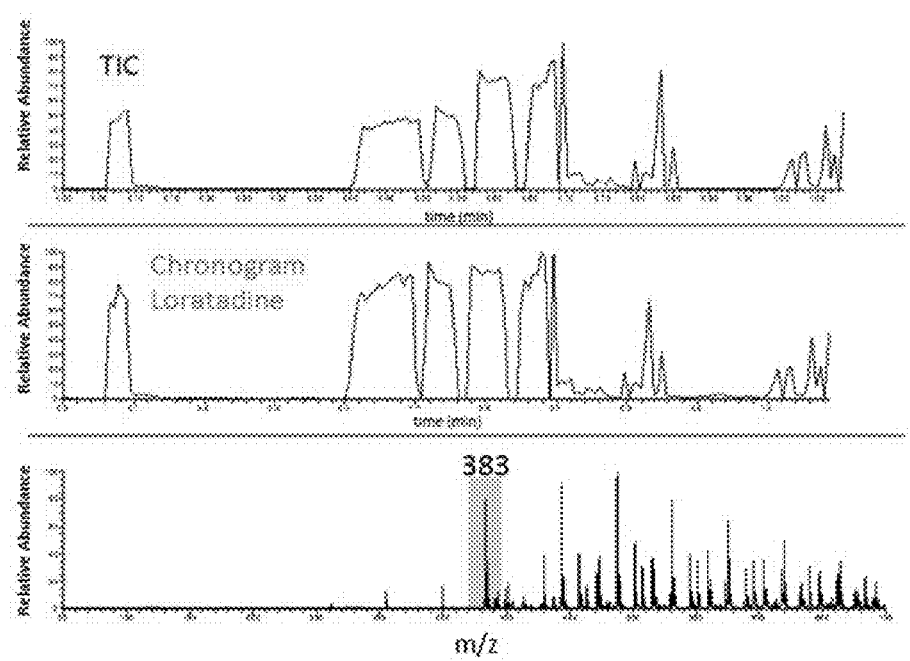
FIG. 10 shows a full mass spectrum of surface contaminant (0.25 ng/cm$^2$ Loratadine on stainless steel surface) using the embodiment illustrated in FIG. 6.
Figure 11:
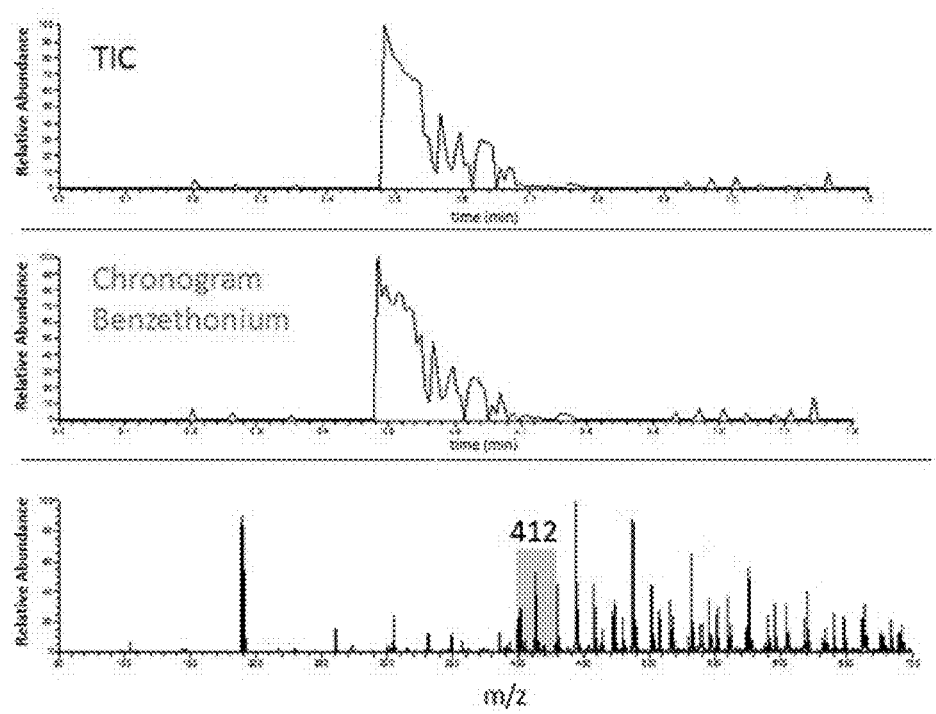
FIG. 11 shows a full mass spectrum of surface contaminant (25 pg/cm$^2$ Benzethonium on stainless steel surface) using the embodiment illustrated in FIG. 6.
Figure 12:
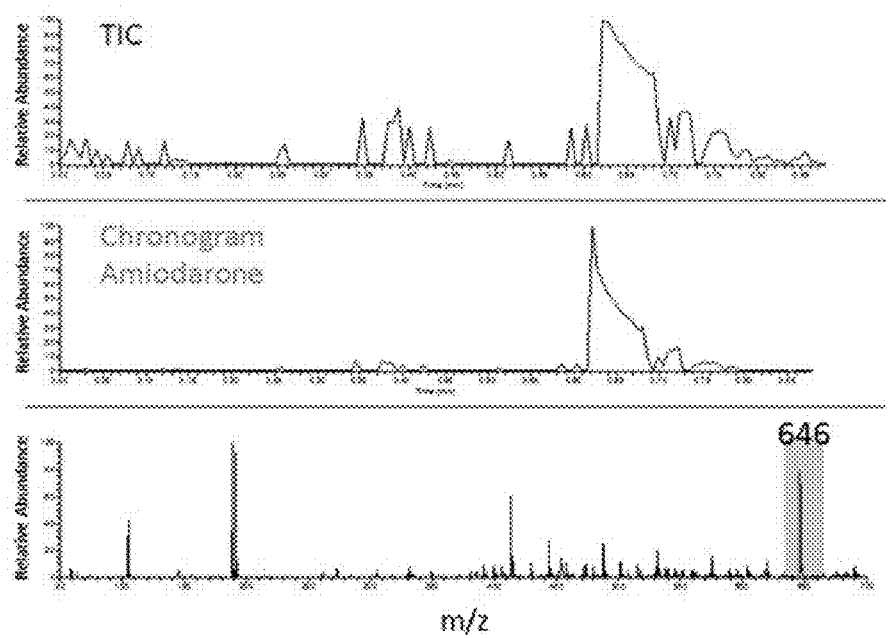
FIG. 12 shows a full mass spectrum of surface contaminant (0.75 ng/cm$^2$ Amiodarone on stainless steel surface) using the embodiment illustrated in FIG. 6.
Figure 13:
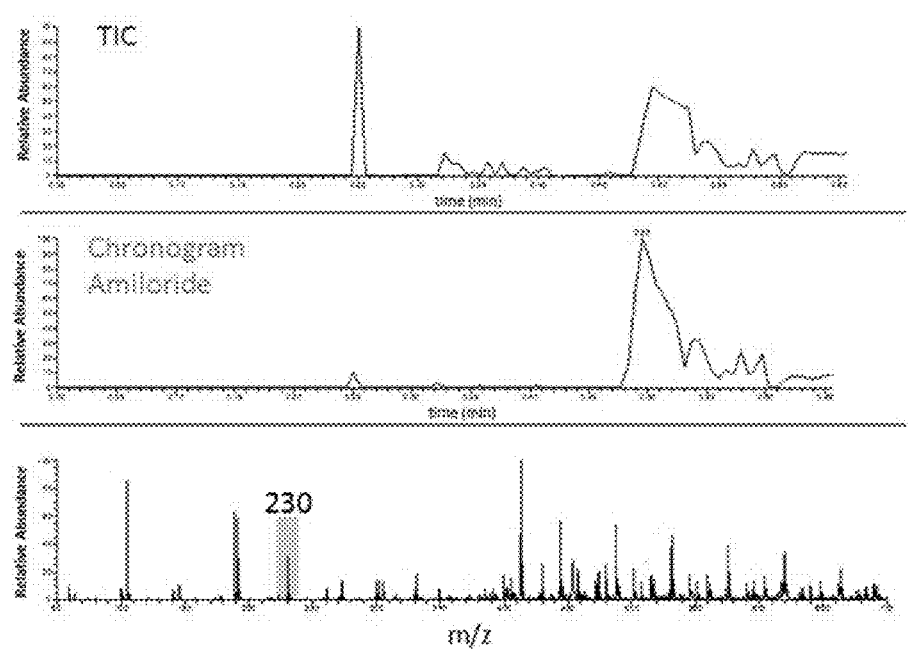
FIG. 13 shows a full mass spectrum of surface contaminant (50 ng/cm$^2$ Amiloride on stainless steel surface) using the embodiment illustrated in FIG. 6.

A system as described in FIG. 6 was used to analyze a surface. A surface interface member was contacted to a surface in a manner in which the porous material on the surface interface member interacted with the surface. In a simultaneous manner, the porous material was wetted continuously (about 1 mL solvent) while swabbing the contaminated surface. The porous material absorbed an analyte from the surface, which analyte was flowed from the porous material through the transfer member to the mass spectrometry probe that was coupled to the transfer member. The flowing was accomplished at least in part by a vacuum pressure created in the system by a pump operably coupled to the system. The removable swabbing head provided an optional alternative to clean a much larger surface. The analyte was analyzed by generating ions of the analyte via the mass spectrometry probe that were transferred to a mass analyzer. FIG. 8-13 show the results of trace analysis of 6 common APIs when no electric field was used to generate the analyte ions. Data was collected onsite in real time. FIG. 7 is a time-based plot (chronograms) showing the schematic outline of this analysis.

Those skilled in the art will recognize that numerous modifications can be made to the specific implementations described above. The implementations should not be limited to the particular limitations described. Other implementations may be possible.

What is claimed is:

1. A system for analyzing an analyte from a surface, the system comprising:
   a. a surface interface member, the member comprising a portion that is configured to receive and retain a porous material that can absorb an analyte from a surface;
   b. a mass spectrometry probe with a transfer line;
   c. a transfer member that operably couples the surface interface member and the mass spectrometry probe; and
   d. a pump operably coupled to the system such that a vacuum pressure generated by the pump transfers an analyte absorbed on the porous material through the transfer line to the mass spectrometry probe.

2. The system according to claim 1, wherein the porous material is a wetted porous material.

3. The system according to claim 1, further comprising a solvent reservoir operably coupled to the surface interface member to thereby supply solvent to the porous material.

4. The system according to claim 1, wherein the porous material is temporarily retained on the surface interface member.

5. The system according to claim 1, wherein the transfer member comprises a splitter that splits a portion of flow through the transfer member to the mass spectrometry probe while a remainder of flow is directed to a receiving vessel.

6. The system according to claim 1, wherein the transfer member comprises a tube.

7. The system according to claim 1, wherein the mass spectrometry probe is selected from the group consisting of: an electrospray probe, a nano electrospray probe, an atmospheric pressure chemical ionization probe, and a probe that generates ions by inductive charging wherein the use of an electric field for high voltage spray ionization is optional.

8. The system according to claim 1, further comprising a mass analyzer, wherein the mass analyzer is part of a miniature mass spectrometer.

9. A validation and verification method of a cleaning process for a surface using the system of claim 8, wherein absence of mass signals of a known contaminant validates and verifies said cleaning process.

10. A validation and verification method of a cleaning process for a surface using the system of claim 8, wherein absence of mass signals of a known contaminant validates and verifies substantial cleanness of said surface.

* * * * *